United States Patent
Simpson et al.

(10) Patent No.: US 6,692,492 B2
(45) Date of Patent: Feb. 17, 2004

(54) DIELECTRIC-COATED ABLATION ELECTRODE HAVING A NON-COATED WINDOW WITH THERMAL SENSORS

(75) Inventors: John A. Simpson, Carlsbad, CA (US); Jeffrey A. Hall, Birmingham, AL (US); Jeffrey A. Calhoun, Temecula, CA (US); Wade A. Bowe, Temecula, CA (US)

(73) Assignee: Cardiac Pacemaker, Inc., St. Paul, MN (US)

( * ) Notice: Subject to any disclaimer, the term of this patent is extended or adjusted under 35 U.S.C. 154(b) by 9 days.

(21) Appl. No.: 09/997,820

(22) Filed: Nov. 28, 2001

(65) Prior Publication Data

US 2003/0100895 A1 May 29, 2003

(51) Int. Cl.$^7$ ............................................. A61B 18/18
(52) U.S. Cl. .......................................... 606/41; 606/42
(58) Field of Search ................................ 606/1, 15, 16, 606/41, 42, 45–50; 600/372, 374

(56) References Cited

U.S. PATENT DOCUMENTS

| | | | |
|---|---|---|---|
| 4,411,266 A | * 10/1983 | Cosman | 606/49 |
| 5,471,982 A | 12/1995 | Edwards et al. | |
| 5,487,385 A | 1/1996 | Avitall | |
| 5,582,609 A | * 12/1996 | Swanson et al. | 606/39 |
| 5,607,422 A | 3/1997 | Smeets et al. | |
| 5,687,723 A | 11/1997 | Avitall | |
| 5,730,127 A | 3/1998 | Avitall | |
| 5,769,847 A | * 6/1998 | Panescu et al. | 606/42 |
| 5,871,523 A | 2/1999 | Fleischman et al. | |
| 5,961,513 A | 10/1999 | Swanson et al. | |
| 5,991,650 A | * 11/1999 | Swanson et al. | 600/374 |
| 6,001,093 A | 12/1999 | Swanson et al. | |
| 6,032,061 A | * 2/2000 | Koblish | 600/372 |
| 6,096,036 A | * 8/2000 | Bowe et al. | 606/41 |
| 6,120,496 A | * 9/2000 | Whayne et al. | 606/1 |
| 6,142,994 A | 11/2000 | Swanson et al. | |
| 6,391,024 B1 | * 5/2002 | Sun et al. | 606/34 |

* cited by examiner

*Primary Examiner*—Michael Peffley
*Assistant Examiner*—Peter Vrettakos
(74) *Attorney, Agent, or Firm*—Fulwider Patton Lee & Utecht, LLP (57) ABSTRACT

A catheter for applying ablation energy to biological tissue having biological fluid flowing thereby includes a shaft having a distal-end region defining a tissue-contacting surface and a fluid-contacting surface. A plurality of band electrodes are positioned at the distal-end region of the shaft. A thermally conductive and non-electrically conductive surface covering, covers a portion of each of the band electrodes substantially coincident with the fluid-contacting surface. Each band electrode thereby has at least one masked portion substantially coincident with the fluid-contacting surface and at least one non-masked portion substantially coincident with the tissue-contacting surface. Ablation energy is transferred through the non-masked portion of the electrode. One or more thermal sensors are located in the non-masked portion of each of the band electrodes.

23 Claims, 6 Drawing Sheets

DIELECTRIC-COATED ABLATION ELECTRODE HAVING A NON-COATED WINDOW WITH THERMAL SENSORS

BACKGROUND OF THE INVENTION

1. Field of the Invention

The invention relates generally to an electrophysiological ("EP") catheter for providing energy to biological tissue within a biological site and, more particularly, to an EP catheter having a dielectric-coated ablation electrode having a non-coated window with thermal sensors.

2. Description of the Related Art

The heart beat in a healthy human is controlled by the sinoatrial node ("SA node") located in the wall of the right atrium. The SA node generates electrical signal potentials that are transmitted through pathways of conductive heart tissue in the atrium to the atrioventricular node ("AV node") which in turn transmits the electrical signals throughout the ventricle by means of the His and Purkinje conductive tissues. Improper growth, remodeling, or damage to, the conductive tissue in the heart can interfere with the passage of regular electrical signals from the SA and AV nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed percutaneously, a procedure in which a catheter is introduced into the patient through an artery or vein and directed to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or to create a conductive tissue block for preventing propagation of the arrhythmia and restoring normal heart function. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the surgical "Maze procedure" involves the formation of continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system providing RF ablation therapy. Migration to a percutaneous catheter approach removes the morbidity associated with a surgically opened chest cavity. In this therapy, transmural ablation lesions are formed in the atria to prevent atrial reentry and to allow sinus impulses to activate the entire myocardium. In this sense transmural is meant to include lesions that pass through the atrial wall or ventricle wall from the interior surface (endocardium) through the cardiac muscle layer (myocardium) to the exterior surface (epicardium).

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In both the unipolar and the bipolar methods, the current traveling between the electrodes of the catheter and between the electrodes and the backplate enters the tissue and induces a temperature rise in the tissue resulting in ablation.

During ablation, RF energy is applied to the electrodes to raise the temperature of the target tissue to a lethal, non-viable state. In general, the lethal temperature boundary between viable and non-viable tissue is between approximately 45° C. to 55° C. and more specifically, approximately 48° C. Tissue heated to a temperature above 48° C. for several seconds becomes permanently non-viable and defines the ablation volume. Tissue adjacent to the electrodes delivering RF energy is heated by resistive heating which is conducted radially outward from the electrode-tissue interface. The goal is to elevate the tissue temperature, which is generally at 37° C., fairly uniformly to an ablation temperature above 48° C., while keeping both the temperature at the tissue surface and the temperature of the electrode well below 100° C. In clinical applications, the target temperature is set below 65° C. to minimize coagulum formation. Lesion size has been demonstrated to be proportional to temperature and duration of ablation.

Blood coagulation is a major limitation/complication associated with RF ablation therapy. Coagulation can lead to thromboembolism and can also form an insulating layer around the electrode hindering further energy delivery required for ablation therapy. Heat appears to be a major factor in the formation of blood coagulum on a catheter electrode. During a typical RF energy ablation procedure using an EP catheter, one or more electrodes carried by the catheter are positioned such that a portion of the electrode(s) are in contact with the tissue being ablated while the remaining portion of the electrodes are in contact with blood. The RF energy applied during the procedure resistively heats the tissue which in turn heats the electrode through conduction. As blood stays in contact with the heated electrode, platelet activation and protein binding occur. This platelet activation appears to be a pathway to coagulum formation.

To reduce the possibility of coagulum formation, one or more thermal sensors may be positioned on the electrodes. Temperature readings provided by the sensors are used to monitor the temperature of the electrodes and to automatically control the power delivered to the electrodes in order to maintain the temperature at or below a target temperature. This type of temperature control scheme assumes that the temperature readings provided by the thermal sensors accurately reflect the temperature at the interface between the electrode and the tissue. This may not, however, be the case, particularly when band electrodes are being used or when thermal sensor orientation to the tissue interface is less than optimum.

During an ablation procedure using a band electrode, only a portion of the band electrode contacts the tissue. Depending on the orientation of the band electrode relative to the tissue and the position of the thermal sensor relative to the band electrode, the thermal sensor may not coincide with that portion of the electrode which contacts the tissue. In this situation, the temperature readings provided by the thermal sensor do not reflect the temperature at the electrode/tissue interface and instead more likely reflect the temperature of the blood pool surrounding the electrode. Power delivery control based on such temperatures may lead to overheating of the electrode/tissue interface and the formation of coagulum.

Hence, those skilled in the art have recognized a need for providing an EP catheter capable of significantly reducing the possibility of coagulum due to electrode overheating regardless of the position of the thermal sensor relative to the tissue. The invention fulfills these needs and others.

SUMMARY OF THE INVENTION

Briefly, and in general terms, the invention is directed to an ablation catheter having one or more electrodes partially coated with a dielectric material. The non-coated portion of the electrode defines a window through which ablation energy is transferred. One or more thermal sensors are located within the window to provide temperature readings.

In one aspect, the invention relates to an ablation catheter including a shaft carrying at least one electrode. A thermally conductive and non-electrically conductive surface covering covers a portion of the electrode. The electrode thus has at least one masked, or coated, portion and at least one non-masked, or non-coated, portion. The catheter further includes at least one thermal sensor located in a non-masked portion of the electrode.

The surface covering serves several purposes. It acts as an electrical insulator to prevent alternate or non-intended site ablations, as the electrode only produces a lesion through the non-coated portion of the electrode, i.e., the ablation window. When the electrode is positioned such that RF energy passes through the ablation window to tissue, the surface covering ensures that no RF energy passes through portions of the electrode that do not contain thermal sensors, thereby ensuring that the electrode/tissue interface will possess accurate temperature readings. The surface covering also acts as a thermal conductor to allow for heat to dissipate from the electrode into the surrounding blood pool. The surface covering allows ablation procedures to be performed using less energy since all the power to the electrode is directed through the ablation window, thus minimizing wasted power. Without an ablation window as such, it is possible for the thermal sensors to be misoriented with respect to the actual electrode/tissue interface. If so, then the temperature readings will be lower than the actual interface temperature. This produces ambiguity that is difficult or impossible to resolve and may promote the formation of coagulum.

In a detailed aspect, the surface covering includes a dielectric material. In further detailed aspects, the dielectric material includes one of parylene, polyimide, polytetrafluoroethylene (PTFE), epoxy, polyurethane, polyester and cyanoacrylate and the surface covering has a thickness in the range of approximately 0.001 to 0.05 millimeters. In another detailed facet, the at least one electrode is a band electrode having a width and a circumference and the surface covering covers the width of the electrode and wraps around a portion of the circumference. In a further detailed facet, the surface cover wraps around approximately one-half to three-fourths of the circumference. In another detailed aspect, the thermal sensor comprises a thermocouple having at least two temperature leads electrically coupled to the non-masked portion of the electrode.

In another aspect, the invention relates to a catheter for applying energy to biological tissue having biological fluid flowing thereby. The catheter includes a shaft having a distal-end region defining a tissue-contacting surface and a fluid-contacting surface. A plurality of band electrodes are positioned at the distal-end region of the shaft. A thermally conductive and non-electrically conductive surface covering covers a portion of each of the band electrodes substantially coincident with the fluid-contacting surface. Each band electrode thereby has at least one masked portion substantially coincident with the intended fluid-contacting surface and at least one non-masked portion substantially coincident with the tissue-contacting surface. The catheter also includes a plurality of thermal sensors. At least one thermal sensor is located in a non-masked portion of each of the band electrodes.

In a detailed facet of the invention, a plurality of thermal sensors are located in the non-masked portion of some of the band electrodes. In a more detailed facet there are two thermal sensors located approximately 60 degrees apart along the circumference of the non-masked portion of the band electrode.

In another aspect, the invention relates to an RF ablation system for applying energy to biological tissue having biological fluid flowing thereby. The system includes a catheter having a shaft having a distal-end region defining a tissue-contacting surface and a fluid-contacting surface. The catheter also includes at least one electrode positioned at the distal-end region of the shaft and a thermally conductive and non-electrically conductive surface covering that covers a portion of the electrode substantially coincident with the fluid-contacting surface. The electrode thereby has at least one masked portion substantially coincident with the fluid-contacting surface and at least one non-masked portion substantially coincident with the tissue-contacting surface. The catheter further includes at least one thermal sensor located in a non-masked portion of the electrode and adapted to provide temperature signals indicative of the temperature at the electrode. The system further includes a power generator adapted to provide power to the at least one electrode and a processor adapted to receive the temperature signals from the at least one thermal sensor and control the provision of power by the power generator based on the signals.

In a more detailed aspect, the catheter includes a plurality of electrodes, each having at least one thermal sensor associated therewith, the power generator is adapted to provide power to each of the electrodes based on the temperature signals from that electrode, and the processor is adapted to control the provision of power to each of the electrodes.

These and other aspects and advantages of the invention will become apparent from the following detailed description and the accompanying drawings which illustrate by way of example the features of the invention.

DETAILED DESCRIPTION OF THE PREFERRED EMBODIMENTS

Figure 1:
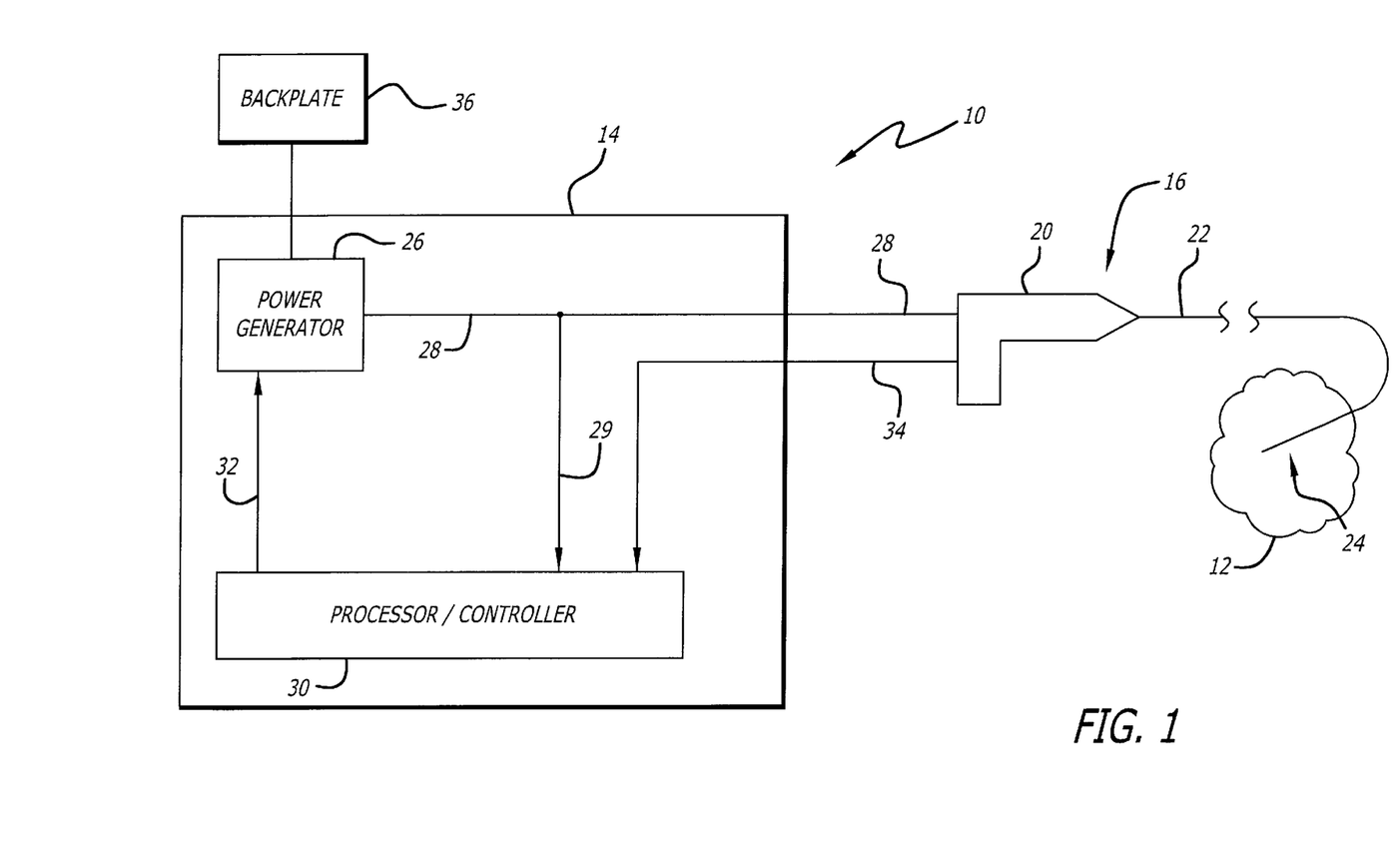
FIG. 1 is a schematic block diagram of an ablation system including a power control system ("PCS") and a catheter system configured in accordance with aspects of the invention.

Turning now to the drawings, in which like reference numerals are used to designate like or corresponding elements among the several figures, in FIG. 1 there is shown a system 10 for use in ablation therapy of a biological site 12, e.g., the atrium or ventricle of the heart. The system 10 includes a power control system 14 and a catheter system 16. The catheter system 16 includes a handle 20 and a steerable catheter shaft 22 having a distal segment 24. The distal segment 24 carries an electrode system (not shown) and is capable of being percutaneously introduced into a biological site 12.

The power control system 14 includes a power generator 26, that may have any number of output channels through which it provides power or drive 28 to the catheter system 16. The operation of the power generator 26 is controlled by a processor/controller 30 which outputs control signals 32 to the power generator 26. The processor/controller 30 monitors the power 28 provided by the power generator 26 along a power monitor line 29. In addition, the processor/controller 30 also receives temperature signals 34 from the catheter system 16. Based on the power 28 and the temperature signals 34, the processor/controller 30 adjusts the operation of the power generator 26.

The system 10 may further include one or more backplates 36 or ground pad electrodes. The backplates 36 or ground pad electrodes are connected to the power generator 26 and generally provides a return path for the power 28 delivered to the biological site 12 through the catheter system 16. Backplates 36 or ground pad electrodes are currently available as self adhesive pads with an electrically conductive gel region and are typically affixed to an exterior surface of the biological subject.

Figures 2, 3:
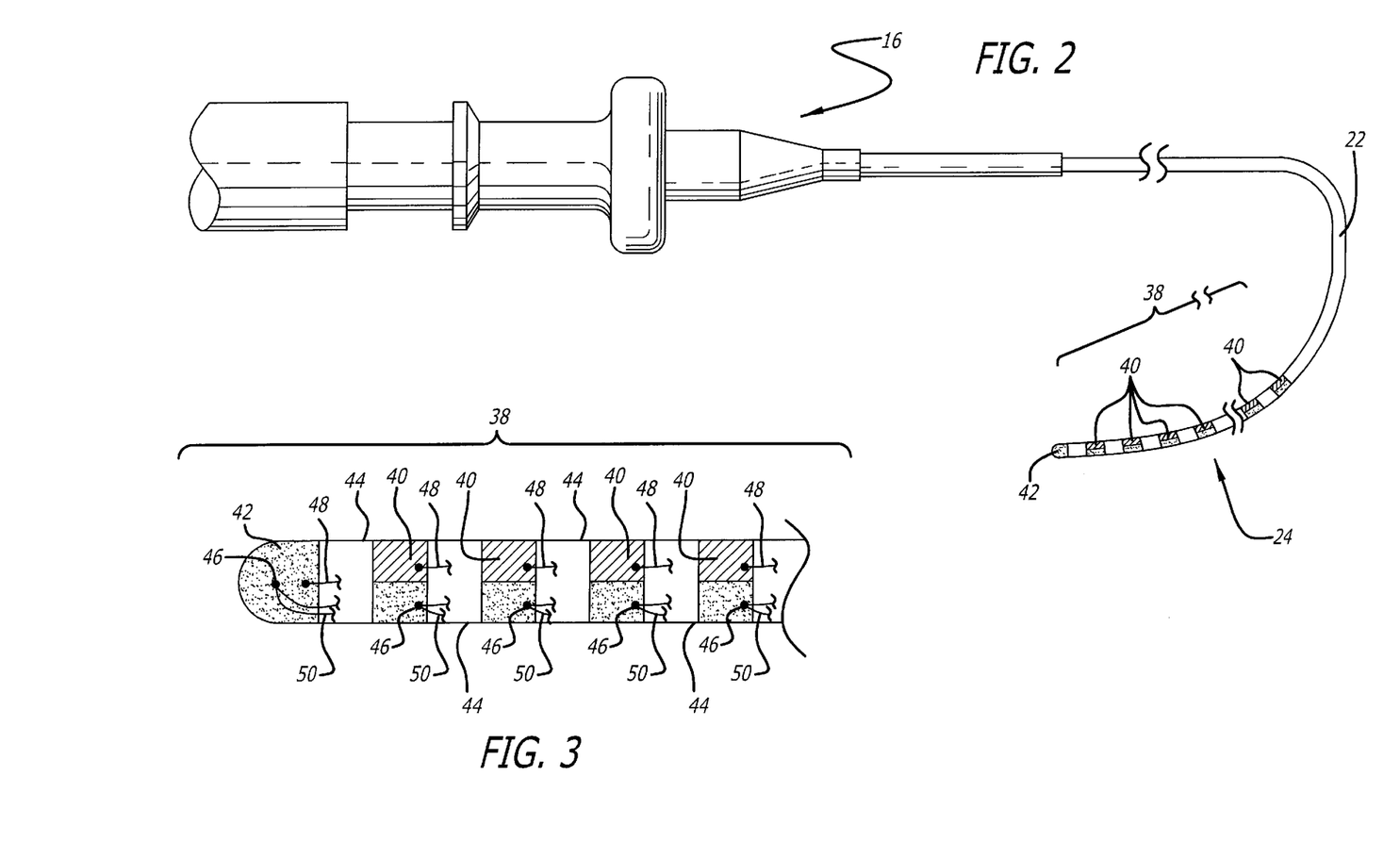
FIG. 2 is a diagram of the catheter system of FIG. 1 presenting more detail including a handle and a catheter shaft having a preformed distal segment carrying a linear array of electrodes having surface coverings.
FIG. 3 is a detailed schematic block diagram of a portion of the distal segment of the catheter system of FIG. 2, depicting a tip electrode and several band electrodes.

As shown in FIGS. 2 and 3, the distal segment 24 of the catheter system 16 includes an electrode system 38. In FIG. 3, the electrode system 38 is shown in schematic form with the components drawn in more detail to more clearly illustrate the relationship between the components. A preferred embodiment of the electrode system 38 includes twelve band electrodes 40 arranged in a substantially linear array along the distal segment 24 of the catheter shaft 22. The electrode system 38 may include a tip electrode 42. (For clarity of illustration, only six band electrodes 40 are shown in FIG. 2 and only four band electrodes 40 are shown in FIG. 3 although as stated, a preferred embodiment may include many more.) The band electrodes 40 are arranged so that there is an electrically non-conductive space 44 between adjacent electrodes. In one configuration of the electrode system 38, the width of the band electrodes 40 is 3 mm and the space 44 between the electrodes is 4 mm. The total length of the electrode system 38, as such, is approximately 8 cm for twelve band electrodes.

The arrangement of the band electrodes 40 is not limited to a linear array and may take the form of other patterns. A substantially linear array is preferred for certain therapeutic procedures, such as treatment of atrial fibrillation, in which linear lesions of typically 4 to 8 cm in length are desired. A linear array is more easily carried by the catheter shaft 22 and also lessens the size of the catheter.

The band electrodes 40 and tip electrode 42 are formed of a material having a significantly higher thermal conductivity than that of the biological tissue to be ablated. Possible materials include silver, gold, chromium, aluminum, molybdenum, tungsten, nickel, platinum, and platinum/10% iridium. Because of the difference in thermal conductivity between the electrodes 40, 42 and the tissue, the electrodes cool off more rapidly in the flowing fluids at the biological site. The band electrodes 40 are sized so that the surface area available for contact with fluid in the heart, e.g., blood, is sufficient to allow for efficient heat dissipation from the electrodes to the surrounding blood. In a preferred embodiment, the electrodes 40 are 7 French (2.3 mm in diameter) with a length of 3 mm and a thickness in the range of about 0.002 mm to about 0.020 mm.

Associated with the electrode system 38 are thermal sensors 46 for monitoring the temperature of the electrode system 38 at various points along its length. In one embodiment, each electrode 40, 42 has a thermal sensor 46 mounted to it. Each thermal sensor 46 provides a temperature signal 34 (FIG. 1) to the processor/controller 30 which is indicative of the temperature of the respective band electrode 40 (FIGS. 2 and 3) at that sensor. In another embodiment of the electrode system 38 a thermal sensor 46 is mounted on every other band electrode 40. Thus for a catheter having twelve electrodes, there are thermal sensors on six electrodes. In yet another embodiment of the electrode system 38 the odd numbered electrodes have one thermal sensor 46 while the even numbered electrodes have two thermal sensors. In still another embodiment there are two thermal sensors on each electrode. In FIG. 3, which shows an embodiment having one thermal sensor for each electrode, there is shown a single power lead 48 for each electrode 40 to provide power to each electrode for ablation purposes and two temperature leads 50 for each thermal sensor 46 to establish a thermocouple effect. In alternate embodiments, the thermal sensors 46 may include thermistors, resistance temperature detectors (RTD) and fluoroptic probes.

With reference to FIG. 1, the temperature signals 34 provided by the electrode thermal sensors 46 (FIG. 3) are used by the processor/controller 30 to monitor the electrodes 40 for unacceptable temperature conditions. Such conditions are described in detail in U.S. application Ser. No. 09/738,032, the disclosure of which is hereby incorporated by reference. For example, in one configuration of the system, if the measured temperature at the interface between the tissue and an electrode 40 is between 5° C. and 9° C. greater than a target temperature programmed in the processor/controller 30, a control signal 32 is sent to the power generator 26 to reduce the peak-to-peak amplitude and/or duty cycle of the power signal 28 being sent to the particular electrode to allow the electrode-tissue interface temperature to cool off. Once the interface is cooled off, the processor/controller 30, may if necessary, incrementally increases the peak-to-peak amplitude and/or duty cycle of the power signal 28, thereby increasing the power to the electrode 40 until the electrode-tissue interface temperature settles to a temperature near the target temperature.

In general, the processor/controller 30 is programmed to control the power such that the closer the electrode-tissue interface temperature is to the target temperature the lesser the rate of change of the peak-to-peak amplitude and/or duty cycle of the power signal 28. For example, if the measured temperature is 20° C. less than the target temperature, the peak-to-peak amplitude and/or duty cycle may be set relatively high in order to increase the electrode-tissue interface temperature rapidly. As the measured temperature increases and the difference between it and the target temperature becomes smaller, the peak-to-peak amplitude and/or duty cycle may be reduced in order to settle in on the target temperature and to avoid exceeding the target temperature by a predetermined amount.

Figure 4:
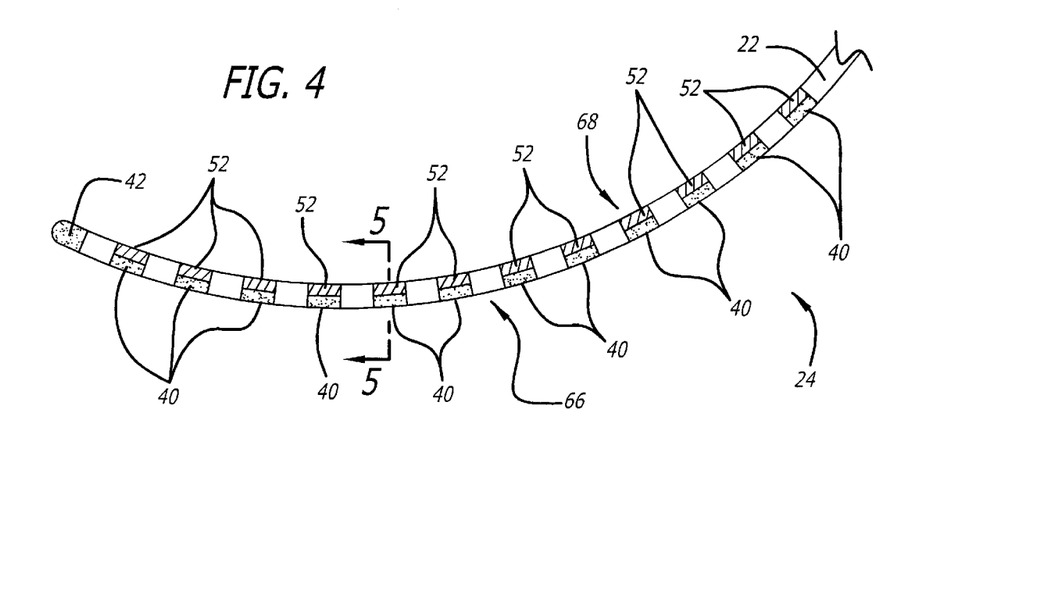
FIG. 4 is a diagram of the distal segment of the catheter system of FIG. 2 showing the coated and non-coated surface areas of the electrodes.

With reference to FIG. 4, in one catheter configuration the distal segment 24 of a deflected catheter shaft 22 has an outer surface 66 and an inner surface 68 with respect to the inherent curvature of the distal segment. During ablation procedures, it is intended that the catheter shaft 22 be oriented such that the outer surface 66 contacts the biological tissue undergoing ablation and the inner surface 68 lies within the blood pool. In accordance with the invention one or more of the electrodes 40, 42 are partially coated or masked with any one of a variety of thermally conductive and non-electrically conductive surface coverings 52.

Figure 5:
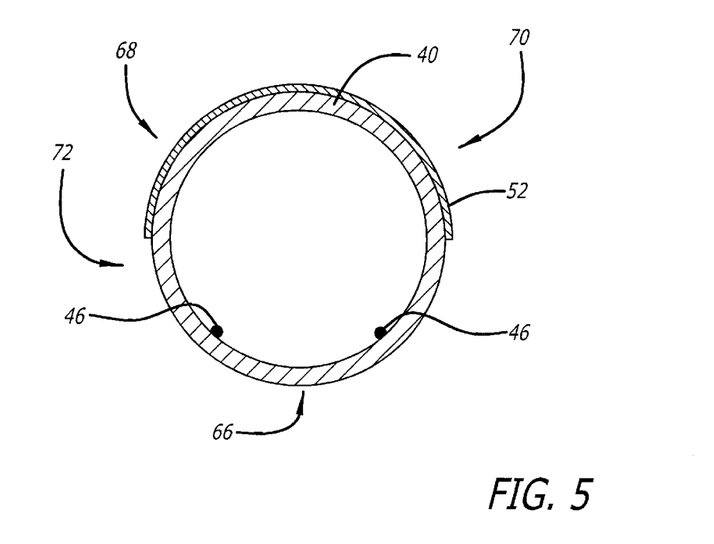
FIG. 5. is a cross-sectional view of one configuration of a band electrode of FIG. 4 along line 5—5, depicting a surface covering wrapping around approximately one-half of the circumference of the band electrode thereby leaving one-half of the circumference uncovered to form an ablation window.

With reference to FIG. 5, in one configuration, the surface covering 52 wraps around approximately one half of the circumference of the electrode 40 thus leaving one half of the electrode exposed. The thickness of the surface covering 52 relative to the thickness of the electrode 40 is not to scale in the figure. The surface covering 52 is applied to the electrode 40 such that it is located on the portion of the electrode coincident with the inner surface 68 thereby placing it within the blood pool when the catheter shaft 22 is oriented as intended. This portion of the electrode 40 is referred to as the masked portion 70. The non-masked portion 72 of the electrode 40 is coincident with the outer surface 66 thereby placing it in contact with the tissue. The non-masked portion 72 of the electrode 40 is also referred to as an ablation window.

As previously mentioned, the electrode system 38 (FIG. 3) includes thermal sensors 46. In accordance with the present invention and as shown in FIG. 5, one or more of these thermal sensors 46 are located within the ablation window 72. In one embodiment, such as shown in FIG. 5, two thermal sensors 46 are positioned approximately 60 degrees apart. As previously mentioned, the thermal sensors 46 maybe thermocouples. In such a configuration, the thermocouple leads are electrically coupled to the inside surface of the band electrode 40, within the ablation window 72, to thereby establish the thermocouple effect. In a preferred embodiment, two thermocouples are formed using only three leads, one of which also functions as the power lead, such as described in U.S. Pat. No. 6,042,580, the disclosure of which is hereby incorporated by reference. With the thermal sensors 46 positioned within the ablation window 72 as such, the temperatures measured by the thermal sensors closely represent the temperature at the outer surface of the ablation window.

Figure 6:
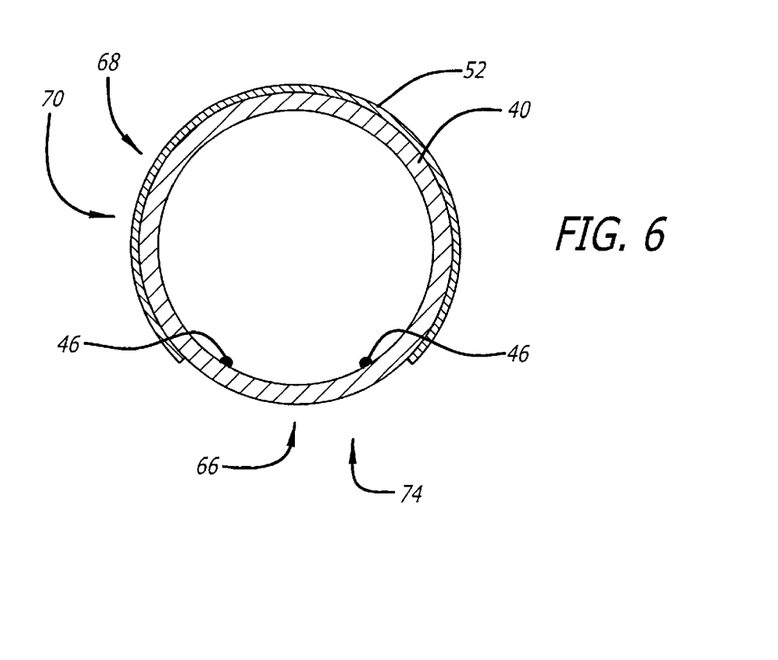
FIG. 6 is a cross-sectional view of an alternate configuration of a band electrode of FIG. 4 along line 5—5, depicting a surface covering wrapping around approximately three-fourths of the circumference of the band electrode thereby leaving one-fourth of the circumference uncovered to form an ablation window.

With reference to FIG. 6, in another configuration, the surface covering 52 wraps around approximately three-fourths of the circumference of the electrode 40 thus leaving a one-fourth circumference ablation window 74. The thermal sensors 46 are located within the ablation window 74. Although configurations having one-half and three-fourths surface coverings 52 have been described, the invention is not limited to such covering sizes. The surface coverings 52 may range from between approximately one-half circumference to three-fourths circumference and may even extend outside of this range. In addition, while the surface coverings 52 have been shown to be continuous around the electrode circumference, they may be discontinuous, with intermittent gaps of exposed electrode defining a plurality of ablation windows. Also, the application of the surface covering 52 is not limited to band electrodes 40. A surface covering 52 may be applied to other shaped electrodes including tip electrodes and flat surface electrodes.

In one embodiment, the surface covering 52 is a thin layer of dielectric material selected from the groups consisting of parylene, polyimide, polytetrafluoroethylene (PTFE), epoxy, polyurethane, polyester and cyanoacrylate. The thickness of the surface covering 52 is in the range of 0.001 to 0.05 millimeters. The surface covering 52 is purposely thin so it does not adversely impact the transfer of heat from the electrode 40 to the surrounding blood pool and is thus thermally conductive. In one preferred embodiment, a UV-curable formulation of cyanoacrylate, Locite 4305, is applied to the electrode 40 and cured by UV exposure. Excess material is removed by machining or microblasting. This formulation of cyanoacrylate has a thermal conductivity of about 0.1 W/m ° C. and a dielectric strength of about 850 volts/mil. The surface covering 52 may be applied to the electrodes 40 prior to assembly of the catheter or after assembly of the catheter. In either case masking is applied to the area where no surface covering 52 is desired. Masking techniques are well known to those skilled in the art, accordingly details of such techniques are not provided.

Figure 7:
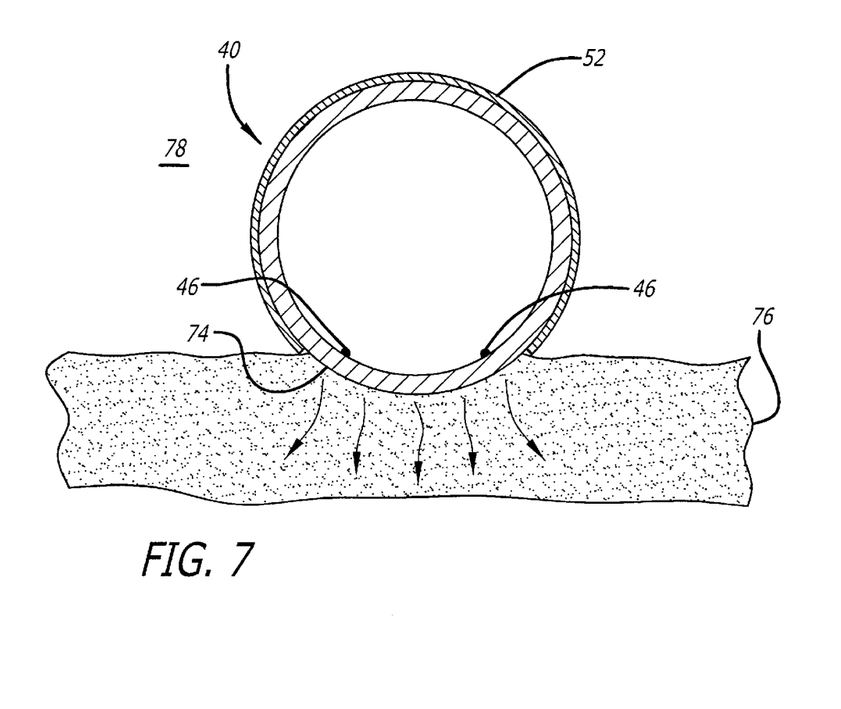
FIG. 7 depicts the band electrode of FIG. 6 oriented relative to a tissue area such that the ablation window contacts the tissue.
Figure 8:
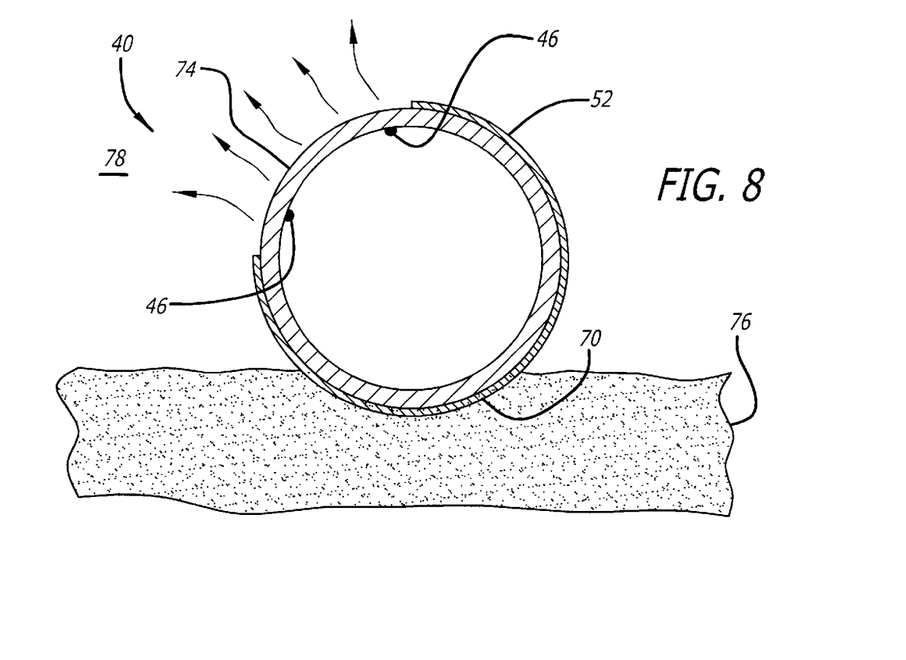
FIG. 8 depicts the band electrode of FIG. 6 oriented relative to a tissue area such that the ablation window lies within the blood pool.
Figure 9:
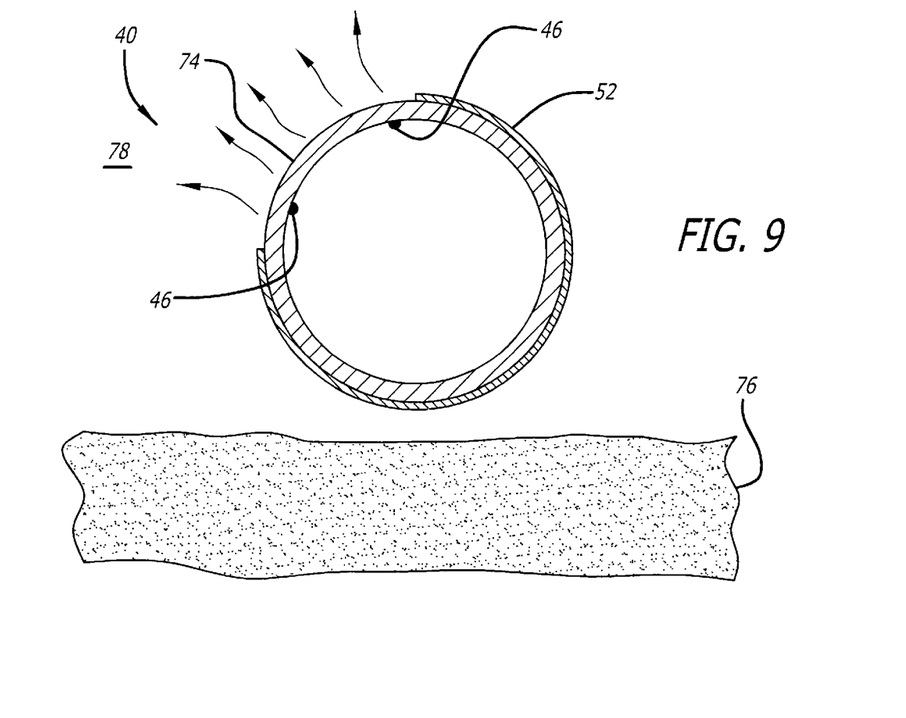
FIG. 9 depicts the band electrode of FIG. 6 oriented relative to a tissue area such that no portion of the electrode contacts the tissue.

With reference to FIGS. 7, 8 and 9, during use the electrode 40 may be oriented such that the ablation window 74 contacts the tissue 76, as shown in FIG. 7, or lies within the blood pool 78, as shown in FIGS. 8 and 9. If the ablation window 74 makes contact with the tissue 76, then the tissue heats resistively during the passage of RF energy through the ablation window 74. Due to the dielectric nature of the surface covering 52, the passage of RF energy from the electrode 40 is confined to the ablation window 74, as indicated by the arrowhead lines. In turn, the tissue-contacting surface of the electrode 40, i.e., the ablation window 74, absorbs heat from the tissue 76, producing a rise in temperature that is readily perceived by the underlying thermal sensors 46. Heat absorbed by the electrode 40 at the interface between the ablation window 74 and the tissue 76 conducts throughout the electrode and is removed by the surrounding blood pool 78 through the thermally conductive surface covering 52.

The process of heat dissipation from the electrode 40 into the blood pool 78 is dependent upon local blood flow conditions, the thickness of both the electrode and its surface covering 52 and the thermal conductively of the electrode and surface covering. Greater heat dissipation is generally preferable because higher levels of RF energy can be delivered through the ablation window 74 without overheating the ablation-window/tissue interface and higher levels of RF energy generally provide greater lesion depth. Minimizing the overheating of the ablation-window/tissue interface (which is generally maintained at a temperature less than 65° C. through thermal sensor feedback control) reduces the incidence of tissue welding, platelet aggregation, char formation and other high temperature biological changes. Minimizing these changes may improve device safety operations in the biological cardiac environment. To maximize heat dissipation, the surface covering 52 is relatively thin and thus possesses adequate thermal conductivity. In this regard, it is significant to note that the surface covering 52 is not thermally insulating.

With reference to FIG. 8, if the electrode 40 is positioned such that the ablation window 74 lies within the blood pool 78, only a masked portion 70 of the electrode 40 contacts the tissue 76. In this situation no RF energy is transferred directly into the contacting tissue 76 due to the dielectric nature of the surface covering 52. Consequently no significant heating occurs within the tissue 76. Similarly, if the electrode 40 is positioned such that no portion of the electrode 40 makes tissue contact, as shown in FIG. 9, then no significant tissue heating occurs. In either instance the electrode's ablation window 74 is exposed directly to the blood pool 78 and any RF energy delivered through the window is substantially dissipated by the moving blood mass and the thermal sensors 46 located within the ablation window 74 perceive essentially no temperature rise.

With the present invention, the electrode/tissue interface should heat up only when the electrode's ablation window 74 makes direct tissue contact, such as shown in FIG. 7. This temperature rise is reliably perceived by the electrode's thermal sensors 46 due to their position within or near the ablation window. Thus unambiguous temperature readings may be obtained and used by the automatic temperature feedback control feature of the power control system 14 (FIG. 1) to control power delivery to the electrodes 40 and substantially reduce the risk of forming coagulum during ablation due to inadvertent overheating at the electrode/tissue interface.

The surface covering 52 serves several purposes. It acts as an electrical insulator to prevent alternate or non-intended site ablations, as the electrode 40 only produces a lesion through the ablation window 74. When the electrode 40 is positioned such that RF energy passes through the ablation window 74 to the tissue 76, the surface covering 52 ensures that no RF energy passes through portions of the electrode that do not contain thermal sensors, thereby ensuring unambiguous temperature readings from the thermal sensors 46 for use by the power control system. The surface covering 52 also acts as a thermal conductor to allow for heat to dissipate from the electrode 40 into the blood pool 78. The surface covering 52 allows ablation procedures to be performed using less energy since all the power to the electrode 40 is directed through the ablation window 74, thus minimizing wasted power.

Figure 10:
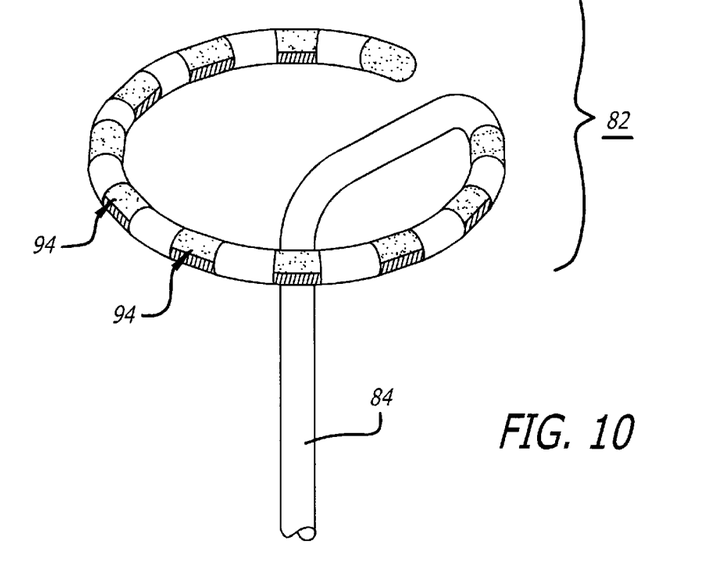
FIGS. 10 and 11 depict an alternate configuration of a catheter with a plurality of band electrodes having a surface covering.
Figure 11:
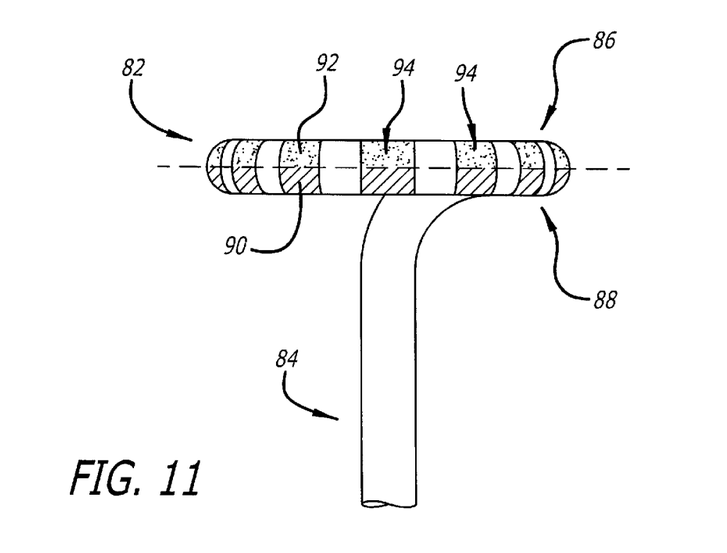

In alternate configurations of catheters employing the covered electrodes of the present invention, the distal-end region of the catheter may have a different shape then that shown in FIG. 4. Common to all such catheters is a shape or configuration that inherently provides a distal-end region having an intended tissue-contacting surface and an intended fluid-contacting surface. The electrodes carried by the distal-end region in turn have an intended tissue-contacting surface and an intended fluid-contacting surface and are covered such that an ablation window is coincident with its intended tissue-contacting surface. For example, as shown in FIGS. 10 and 11, the catheter may have a substantially circular shaped distal-end region 82 lying in a plane substantially perpendicular to the catheter shaft 84. In this catheter, the top-half surface 86, or front-half surface, of the distal-end region 82 defines a tissue-contacting surface. A portion of the top-half surface 86 is intended to contact the biological tissue to be ablated. The bottom-half surface 88, or rear-half surface, of the distal-end region 82 defines a blood-pool surface. A portion of the bottom-half surface 88 is intended to remain in the blood pool during ablation. In accordance with the present invention, a surface covering 90 is applied to the band electrodes 94 at the distal-end region. The surface covering 90 is applied on the portion of the band electrodes 94 coincident with the bottom-half surface 88 thereby typically placing it within the blood pool, while the non-masked portion 92 of the band electrodes 94 is coincident with the top surface 86 thereby placing it in contact with the tissue. The covered electrodes of the present invention may also be used in multi-splined basket catheters such as those disclosed in U.S. Pat. No. 5,575,810.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An ablation catheter comprising:
   a shaft carrying at least one electrode;
   a thermally conductive and non-electrically conductive surface covering having a thickness in the range of approximately 0.001 to 0.05 millimeters that covers a portion of the electrode, the electrode thereby having at least one masked portion and at least one non-masked portion; and
   at least one thermal sensor located in a non-masked portion of the electrode.

2. The catheter of claim 1 wherein the surface covering comprises a dielectric material.

3. The catheter of claim 2 wherein the dielectric material comprises one of parylene, polyimide, polytetrafluoroethylene (PTFE), epoxy, polyurethane, polyester and cyanoacrylate.

4. The catheter of claim 1 wherein the at least one electrode comprises a band electrode having a width and a circumference and the surface covering covers the width of the electrode and wraps around a portion of the circumference.

5. The catheter of claim 4 wherein the surface cover wraps around approximately one-half to three-fourths of the circumference.

6. The catheter of claim 1 wherein the thermal sensor comprises one of a thermocouple, thermistor, resistance temperature detector (RTD) and fluoroptic probe.

7. The catheter of claim 1 wherein the thermal sensor comprises a thermocouple having at least two temperature leads electrically coupled to the non-masked portion of the electrode.

8. The catheter of claim 1 wherein a plurality of thermal sensors are located in the non-masked portion of the electrode.

9. The catheter of claim 8 wherein the electrode is a band electrode and the thermal sensors are located at different points along the circumference of the non-masked portion of the band electrode.

10. The catheter of claim 9 wherein there are two thermal sensors located approximately 60 degrees apart along the circumference of the non-masked portion of the band electrode.

11. A catheter for applying energy to biological tissue having biological fluid flowing thereby, said catheter comprising:

a shaft having a distal-end region defining a tissue-contacting surface and a fluid-contacting surface;

a plurality of band electrodes positioned at the distal-end region of the shaft;

a thermally conductive and non-electrically conductive surface covering comprising a dielectric material having a thickness in the range of approximately 0.001 to 0.05 millimeters that covers a portion of each of the band electrodes substantially coincident with the fluid-contacting surface, each band electrode thereby having at least one masked portion substantially coincident with the fluid-contacting surface and at least one non-masked portion substantially coincident with the tissue-contacting surface; and a plurality of thermal sensors, at least one thermal sensor located in a non-masked portion of each of the band electrodes.

12. The catheter or claim 11 wherein the dielectric material comprises one of parylene, polyimide, polytetrafluoroethylene (PTFE), epoxy, polyurethane, polyester and cyanoacrylate.

13. The catheter of claim 11 wherein each of the band electrodes has a width and a circumference and the surface covering covers the width of the electrode and wraps around a portion of the circumference.

14. The catheter of claim 13 wherein the surface cover wraps around approximately one-half to three-fourths of the circumference.

15. The catheter of claim 11 wherein each of the thermal sensors comprises a thermocouple having at least two leads electrically coupled to the non-masked portion of the band electrode.

16. The catheter of claim 11 wherein a plurality of thermal sensors are located in the non-masked potion of some of the band electrodes.

17. The catheter of claim 16 wherein there are two thermal sensors located approximately 60 degrees apart along the circumference of the non-masked portion of the band electrode.

18. An RF ablation system for applying energy to biological tissue having biological fluid flowing thereby, said system comprising:

a catheter having:
  a shaft having a distal-end region defining a tissue-contacting surface and a fluid-contacting surface;

at least one electrode positioned at the distal-end region of the shaft;

a thermally conductive and non-electrically conductive surface covering comprising a dielectric material having a thickness in the range of approximately 0.001 to 0.05 millimeters that covers a portion of the electrode substantially coincident with the fluid-contacting surface, the electrode thereby having at least one masked portion substantially coincident with the fluid-contacting surface and at least one non-masked portion substantially coincident with the tissue-contacting surface; and at least one thermal sensor located in a non-masked portion of the electrode and adapted to provide temperature signals indicative of the temperature at the electrode;

a power generator adapted to provide power to the at least one electrode; and a processor adapted to receive the temperature signals from the at least one thermal sensor and control the provision of power by the power generator based on the signals.

19. The RF ablation system of claim 18 wherein the catheter includes a plurality of electrodes, each having at least one thermal sensor associated therewith, the power generator is adapted to provide power to each of the electrodes, and the processor is adapted to control the provision of power to each of the electrodes.

20. The catheter of claim 18 wherein the dielectric material comprises one of parylene, polyimide, polytetrafluoroethylene (PTFE), epoxy, polyurethane, polyester and cyanoacrylate.

21. The catheter of claim 18 wherein the at least one electrode comprises a band electrode having a width and a circumference and the surface covering covers the width of the electrode and wraps around a portion of the circumference.

22. The catheter of claim 21 wherein the surface cover wraps around approximately one-half to three-fourths of the circumference.

23. The catheter of claim 18 wherein a plurality of thermal sensors are located in the non-masked portion of the at least one electrode.

* * * * *

UNITED STATES PATENT AND TRADEMARK OFFICE
CERTIFICATE OF CORRECTION

PATENT NO. : 6,692,492 B2
DATED : February 17, 2004
INVENTOR(S) : John A. Simpson et al.

It is certified that error appears in the above-identified patent and that said Letters Patent is hereby corrected as shown below:

Column 11,
Line 34, delete "potion" and insert -- portion --.

Signed and Sealed this

Tenth Day of August, 2004

JON W. DUDAS
*Acting Director of the United States Patent and Trademark Office*